US010758387B2

(12) United States Patent
Roeder et al.

(10) Patent No.: US 10,758,387 B2
(45) Date of Patent: Sep. 1, 2020

(54) ENDOVASCULAR STENT GRAFT ASSEMBLY AND DELIVERY DEVICE

(71) Applicants: Cook Medical Technologies LLC, Bloomington, IN (US); The Cleveland Clinic Foundation, Cleveland, OH (US)

(72) Inventors: Blayne A. Roeder, Bloomington, IN (US); Roy K. Greenberg, Bratenahl, OH (US); Stephan Haulon, Lille (FR)

(73) Assignees: Cook Medical Technologies LLC, Bloomington, IN (US); The Cleveland Clinic Foundation, Cleveland, OH (US)

( * ) Notice: Subject to any disclaimer, the term of this patent is extended or adjusted under 35 U.S.C. 154(b) by 62 days.

(21) Appl. No.: 14/875,925

(22) Filed: Oct. 6, 2015

(65) Prior Publication Data

US 2016/0106564 A1 Apr. 21, 2016

Related U.S. Application Data

(60) Provisional application No. 62/064,595, filed on Oct. 16, 2014.

(51) Int. Cl.
*A61F 2/97* (2013.01)
*A61F 2/07* (2013.01)
(Continued)

(52) U.S. Cl.
CPC ............... *A61F 2/97* (2013.01); *A61F 2/064* (2013.01); *A61F 2/07* (2013.01); *A61F 2/856* (2013.01);
(Continued)

(58) Field of Classification Search
CPC .. A61F 2/064; A61F 2/07; A61F 2/856; A61F 2/954; A61F 2/966; A61F 2/97;
(Continued)

(56) References Cited

U.S. PATENT DOCUMENTS 6,042,605 A 3/2000 Martin
7,413,573 B2 * 8/2008 Hartley ..................... A61F 2/07
623/1.13

(Continued)

FOREIGN PATENT DOCUMENTS

EP           2803340 A1    11/2014
WO    WO 2005/034808 A1    4/2005
(Continued)

OTHER PUBLICATIONS

Partial European Search Report for corresponding EP 15275213, dated Mar. 1, 2016, 4 pages.
(Continued)

*Primary Examiner* — Kathleen S Holwerda
*Assistant Examiner* — Brooke Labranche
(74) *Attorney, Agent, or Firm* — Brinks Gilson & Lione

(57) ABSTRACT

A pre-loaded delivery device that facilitates accurate placement of a stent graft assembly in the aorta is disclosed. A stent graft is carried on the delivery device and held in a pre-deployment configuration by a sheath. A split in the sheath facilitates the pre-cannulation of one or more branch arteries extending from the aorta before the stent graft is fully released in the aorta. The stent graft comprises a tubular body having at least one scalloped fenestration formed in one end of the graft material and at least one fenestration formed in the graft material of the main tubular body. A helical internal side branch extends from the fenestration within the lumen of the main tubular body. The helical side branch is configured to curve at least partially
(Continued)

around the scalloped fenestration. The assembly further comprises a connection stent graft extending from the fenestration into a branch vessel.

15 Claims, 5 Drawing Sheets

(51) Int. Cl.
```
A61F 2/06      (2013.01)
A61F 2/966     (2013.01)
A61F 2/856     (2013.01)
A61F 2/89      (2013.01)
A61F 2/82      (2013.01)
```
(52) U.S. Cl.
CPC ............. *A61F 2/966* (2013.01); *A61F 2/89* (2013.01); *A61F 2002/061* (2013.01); *A61F 2002/072* (2013.01); *A61F 2002/826* (2013.01); *A61F 2002/9665* (2013.01); *A61F 2220/0025* (2013.01)

(58) Field of Classification Search
CPC .......... A61F 2002/061; A61F 2002/072; A61F 2002/9665; A61F 2220/0025; A61F 2002/826; A61F 2/89
See application file for complete search history.

(56) References Cited

U.S. PATENT DOCUMENTS

| | | |
|---|---|---|
| 8,518,098 B2 | 8/2013 | Roeder et al. |
| 8,926,686 B2* | 1/2015 | King .................. A61F 2/07 623/1.13 |
| 2003/0199967 A1* | 10/2003 | Hartley ............... A61F 2/07 623/1.13 |
| 2005/0131518 A1 | 6/2005 | Hartley et al. |
| 2006/0247761 A1* | 11/2006 | Greenberg .......... A61F 2/07 623/1.16 |
| 2007/0233222 A1* | 10/2007 | Roeder ............... A61F 2/95 623/1.11 |
| 2009/0182411 A1 | 7/2009 | Irwin et al. |
| 2010/0100167 A1* | 4/2010 | Bortlein ............. A61F 2/2436 623/1.11 |
| 2013/0131777 A1* | 5/2013 | Hartley .............. A61F 2/07 623/1.11 |
| 2013/0289701 A1 | 10/2013 | Coghlan et al. |
| 2013/0289702 A1 | 10/2013 | Coghlan et al. |

FOREIGN PATENT DOCUMENTS

| | | |
|---|---|---|
| WO | WO 2005/122962 A1 | 12/2005 |
| WO | WO 2008/002426 A1 | 1/2008 |
| WO | WO 2008/057568 A1 | 5/2008 |
| WO | WO 2010/111583 A1 | 9/2010 |
| WO | WO 2011/109067 A1 | 9/2011 |
| WO | WO 2013/104324 A1 | 8/2013 |
| WO | WO 2015/071135 A1 | 5/2015 |
| WO | WO 2015/081175 A1 | 6/2015 |

OTHER PUBLICATIONS

Extended European Search Report for corresponding EP 15275213, dated May 30, 2016, 9 pages.
European Search Report for corresponding European Patent Application No. EP 17166079, dated May 11, 2017, 5 pages.
Examination Report for corresponding European Patent Application No. EP 17166079, dated Oct. 17, 2017, 6 pages.
European Search Report for EP Application No. 18168827.6 dated Jul. 16, 2018, 8 pages.
European Examination Report for EP Application No. 18168827.6 dated Oct. 19, 2018, 6 pages.

* cited by examiner

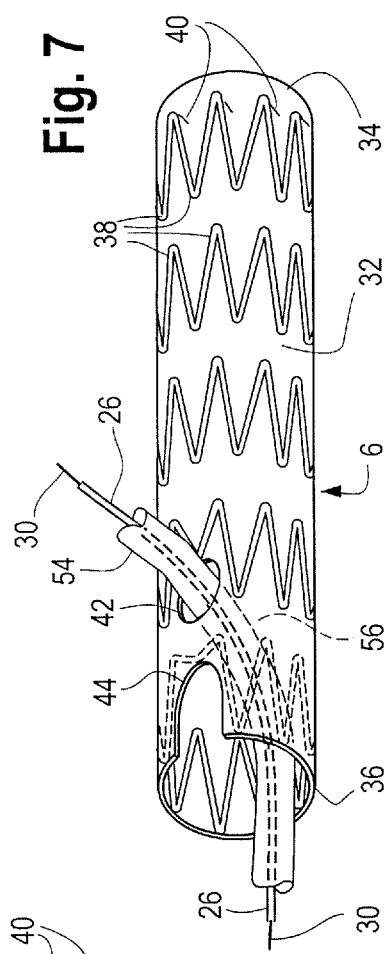
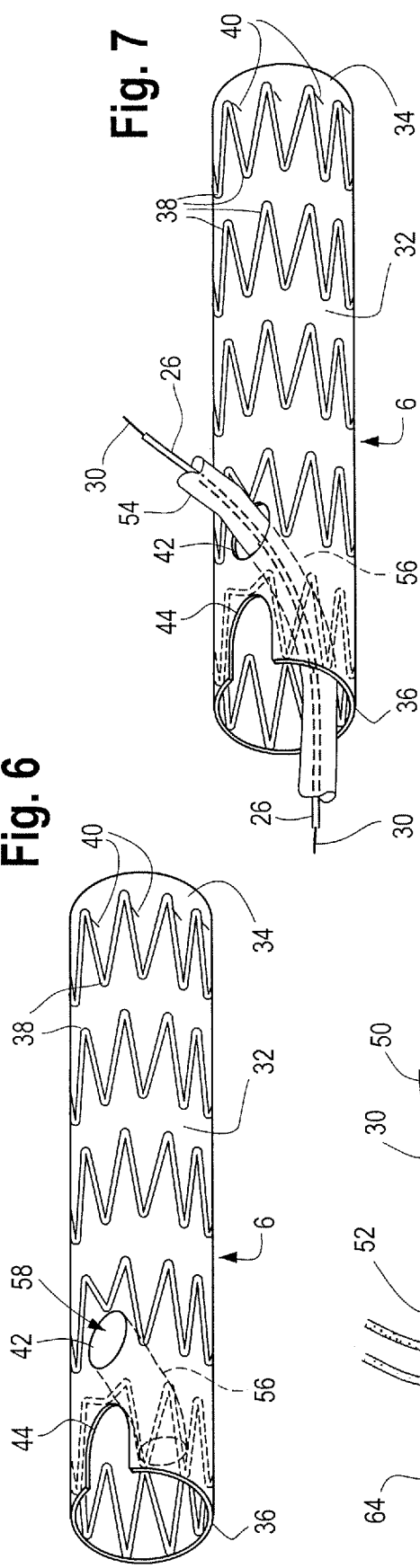
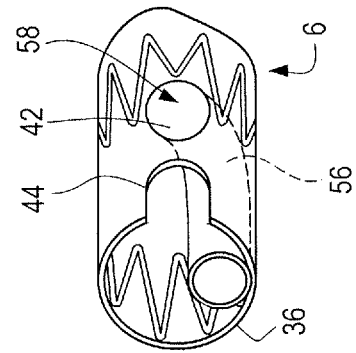
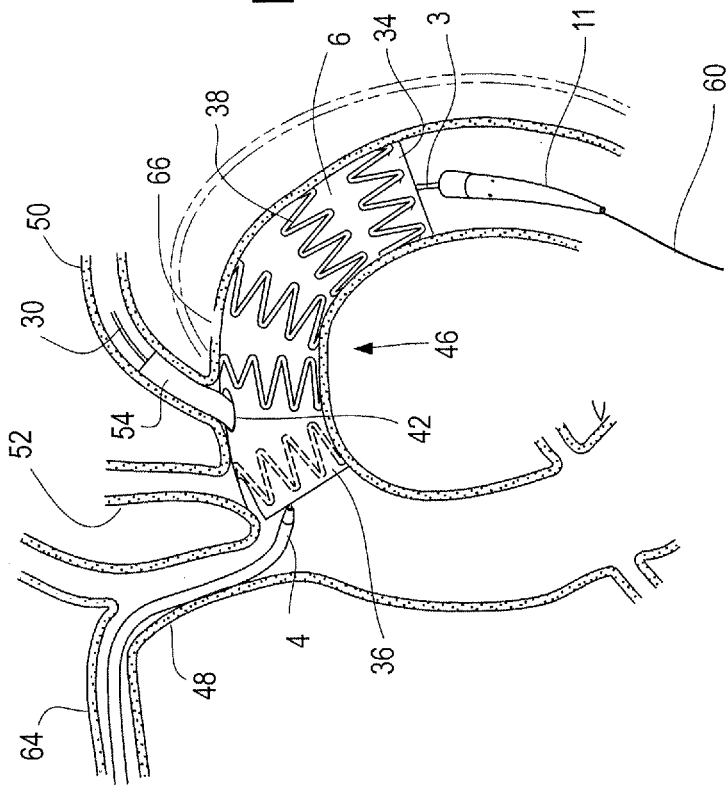

ENDOVASCULAR STENT GRAFT ASSEMBLY AND DELIVERY DEVICE

RELATED APPLICATIONS

The present application claims the benefit of the filing date under 35 U.S.C. § 119(e) of Provisional U.S. Patent Application Ser. No. 62/064,595, filed Oct. 16, 2014, which is hereby incorporated by reference.

BACKGROUND

This invention relates generally to medical devices, and more particularly, to an endovascular stent graft assembly and a delivery device for placement and deployment of the stent graft assembly in a vessel lumen.

Stent grafts may be inserted into an anatomical vessel or duct for various purposes. For example, stent grafts are used for treatment of vasculature in the human or animal body to bypass or repair a defect in the vasculature or to maintain or restore patency in a formerly blocked or constricted passageway. For example, a stent graft may extend proximally and/or distally away from a vascular defect, including a diseased portion such as an aneurysm or dissection, and engage a healthy portion of a vessel wall.

In recent years stent grafts have been developed for treatment of aortic aneurysms and dissections. These devices are delivered to the treatment site through the vascular system of the patient rather than by open surgery. The stent grafts include a tubular or cylindrical framework or scaffolding of one or more stents to which is secured a generally tubular shaped biocompatible graft material such as woven Dacron®, polyester, polytetrafluoroethylene, or the like. The devices are initially reduced to a small diameter and placed into the leading or proximal end of a catheter delivery system. The delivery system is inserted into the vascular system of the patient and maneuvered to the treatment site over a previously positioned guide wire. Through manipulation of a control system that extends along the length of the delivery device to a distal end of the system outside the patient, the stent graft may be deployed at a desired location after withdrawing a surrounding sheath. The stent graft becomes anchored into position to healthy wall tissue in the aorta. The delivery device may then be removed, leaving the stent graft in place and thereby bypassing an aneurysm or dissection in the aorta.

For treatment of thoracic aortic aneurysms and/or dissections in particular, it is necessary to introduce the stent graft high up in the aorta and in a region of the aorta which is curved and where there can be strong blood flow. Furthermore, in the thoracic aorta there are major branch vessels extending therefrom, such as the brachiocephalic, carotid and/or subclavian arteries. During and/or after treatment of an aneurysm or dissection in the region of the thoracic arch, it is desirable for blood supply to continue to flow to these branch arteries. For this purpose, fenestrations or side branches are provided in a stent graft that is placed in that region, through which side arms or branch extensions may be deployed and extend into the brachiocephalic, carotid and/or subclavian arteries, for example.

It has also been recognized that endovascular treatment of diseased vessels can be simplified by use of pre-loaded components such as guide wires, catheters, and/or sheaths. These pre-loaded components can be pre-loaded into a delivery system (e.g., a delivery device or introducer) and/or a prosthetic device (e.g., a stent graft) prior to introduction into a patient to aid in delivery of additional prosthetic devices (e.g., branch extension or side arm prostheses) extending from the main prosthetic device. These pre-loaded components may help to simplify and improve branch vessel cannulation, thereby facilitating accurate placement of a branched stent graft assembly in the aortic arch and descending thoracic aorta and one or more branch arteries extending therefrom.

SUMMARY

The present disclosure describes a system for the delivery and deployment of an endovascular stent graft and also describes a stent graft assembly. In one example, the system comprises a delivery device having a longitudinal axis comprising a pusher catheter having a proximal end and a distal end and defining a lumen extending between the proximal and distal ends. A guide wire catheter extends longitudinally within the lumen of the pusher catheter. A stent graft is releasably coupled to the delivery device. A sheath having a proximal end and a distal end is mounted over the stent graft thereby retaining the stent graft in a radially contracted configuration on the delivery device, the sheath comprising a split located between the proximal and distal ends of the sheath thus forming a distal sheath segment located distal of the split and a proximal sheath segment located proximal of the split. The system further comprises an auxiliary catheter having a proximal end and a distal end and defining a guide wire lumen therebetween through which a guide wire may extend, wherein the auxiliary catheter extends longitudinally under the distal sheath segment and through the sheath split between the proximal and distal sheath segments.

Further described herein is a stent graft. In one example, the stent graft comprises a main tubular body of a biocompatible graft material defining a main lumen having a first end and a second end. There is at least one scalloped fenestration formed in the graft material at the second end and at least one fenestration formed in the graft material of the main tubular body. An internal side branch defining a lumen extends from the fenestration towards the second end of the stent graft within the lumen of the main tubular body, wherein the internal side branch is configured to extend at least partially around the scalloped fenestration.

Also described herein is a stent graft assembly. In one example, the assembly comprises a main stent graft comprising a tubular body of a biocompatible graft material defining a main lumen having a first end and a second end. There is at least one scalloped fenestration formed in the graft material at the second end and at least one fenestration formed in the graft material of the main tubular body. An internal side branch defining a lumen extends from the fenestration towards the second end of the stent graft within the lumen of the main tubular body, wherein the internal side branch is configured to extend at least partially around the scalloped fenestration. The assembly further comprises a connection stent graft comprising a tubular body of a biocompatible graft material defining a main lumen, the connection stent graft extending from the fenestration formed in the main tubular body.

BRIEF DESCRIPTION OF THE DRAWINGS

FIG. 6 illustrates one example of the stent graft having an internal side arm extending from a fenestration in the graft body and around a scalloped fenestration formed in one end of the graft.

FIG. 7 illustrates the placement of an external side branch stent graft extending into the end of the graft of FIG. 6, through the internal side arm, and out of the fenestration.

FIG. 8 illustrates placement and deployment of the stent graft of FIG. 6 in the aorta and placement of an external side branch stent graft extending into a branch artery.

FIG. 9 illustrates an end view of one example of the stent graft having an internal side arm extending from a fenestration in the graft body and around a scalloped fenestration formed in one end of the graft.

DETAILED DESCRIPTION

The present disclosure relates to an endoluminal prosthesis for implantation within a human or animal body for repair of damaged vessels, ducts, or other physiological pathways and systems for delivering such an endoluminal prosthesis. In the present disclosure, when describing a delivery device or introducer, the term "proximal" refers to a direction that is generally farthest from the user during a medical procedure, while the term "distal" refers to a direction that is closest to the user during a medical procedure. When referring to a prosthesis such as a stent graft, the term "first end" may be in reference to a portion of the stent graft which, when carried on the delivery device, is closest to the proximal end of the delivery device, and the term "second end" may be in reference to the end of the stent graft opposite the "first end" (e.g., the end of the stent graft closest to the distal end of the delivery device). The term "ipsilateral" is used to indicate that the diseased vessel(s) being accessed during a given procedure are on the same side of the body (right or left) as the vascular access device while "contralateral" signifies that the vessel(s) of interest are on the opposite side of the body. The term "pre-loaded" as used here means that the "pre-loaded" component is part of the delivery device at the time of use by the user during a procedure.

Figure 1:
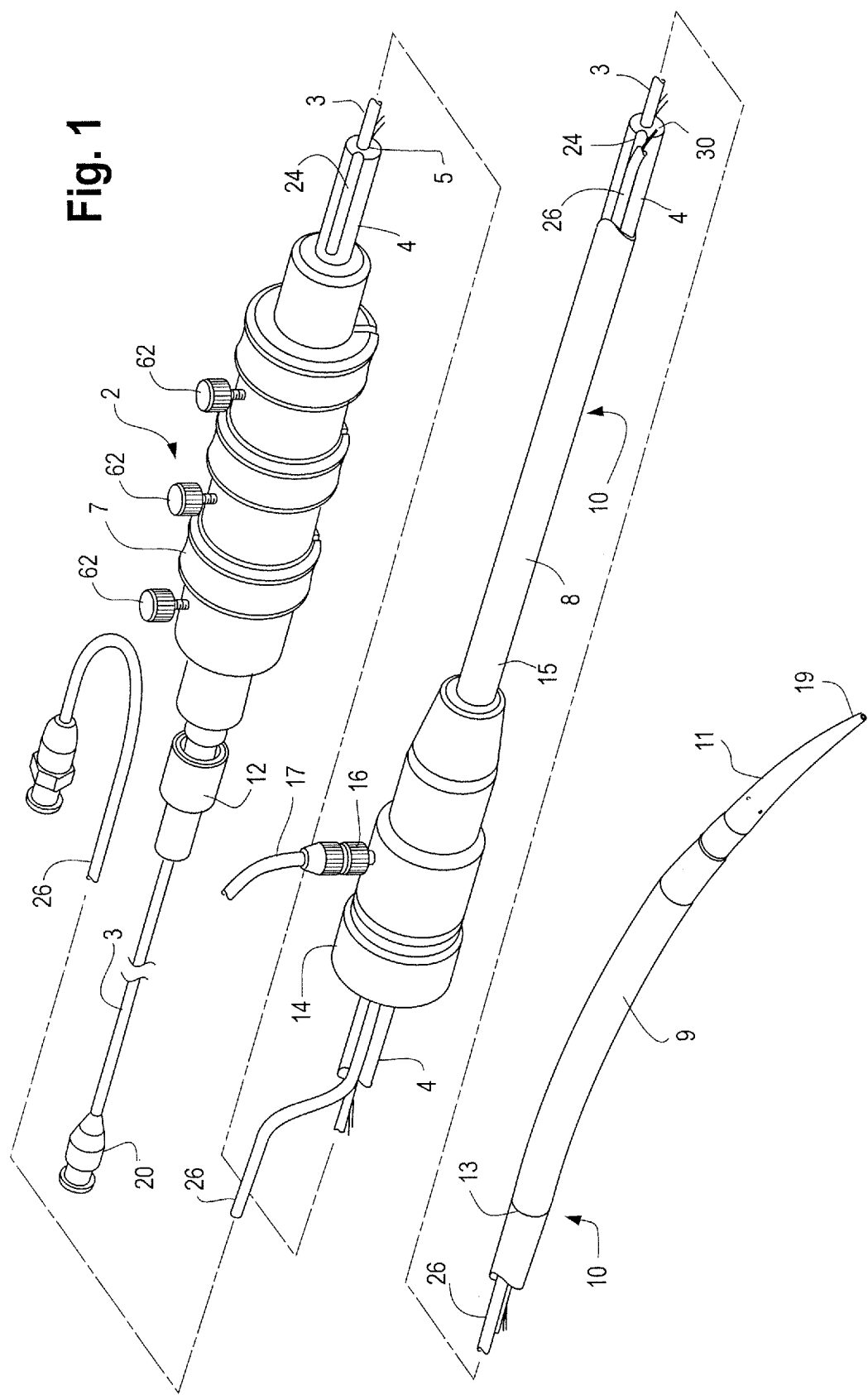
FIG. 1 shows a perspective view of one example of a delivery device with a sheath having a proximal sheath segment and a distal sheath segment covering a stent graft at the proximal end of the device.
Figure 2:
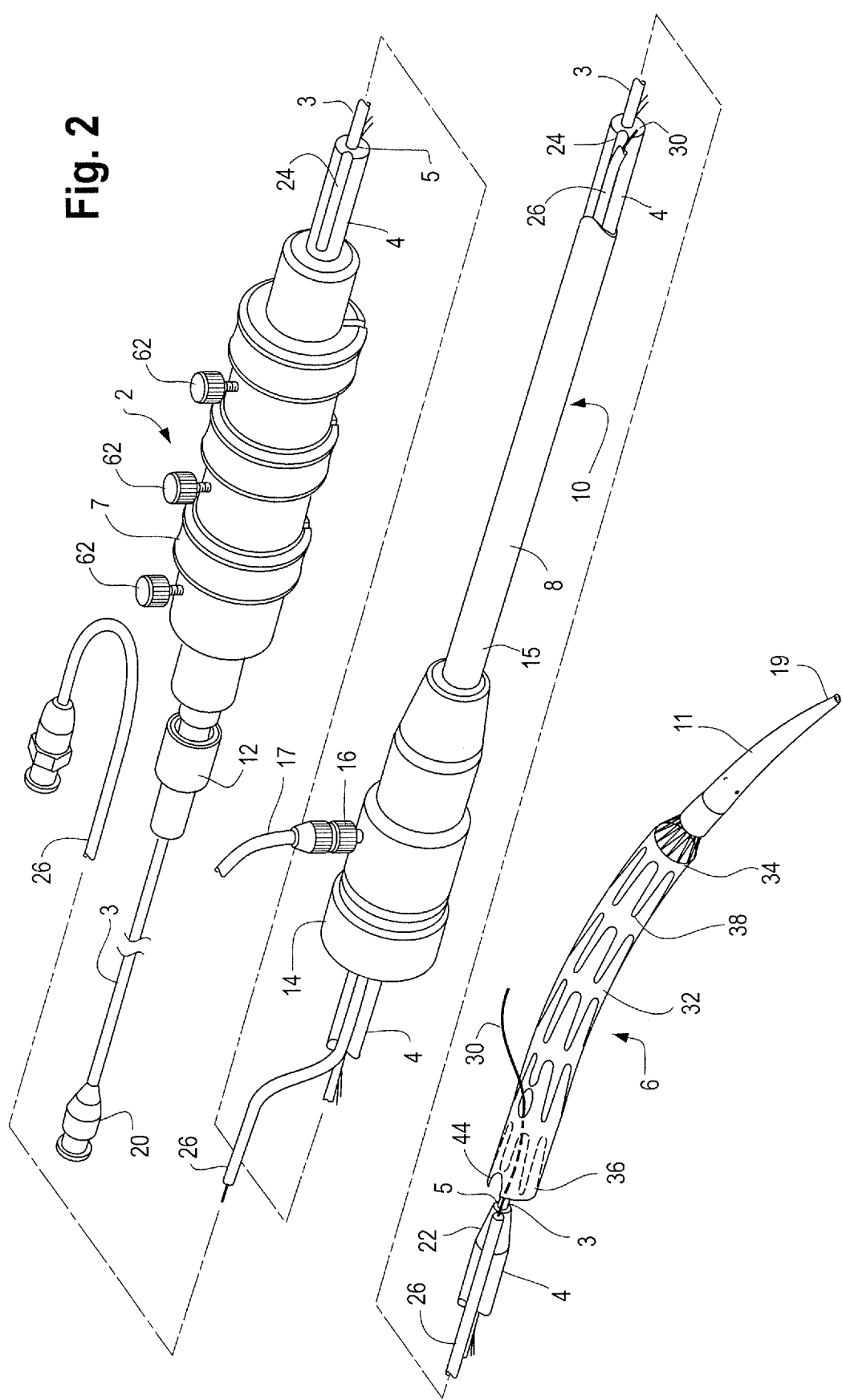
FIG. 2 shows a perspective view of the delivery device of FIG. 1 with the sheath withdrawn to expose the stent graft.

Referring to FIG. 1, an example of a stent graft delivery device is shown generally at 2. FIG. 2 shows the same view as FIG. 1 but with a sheath 10 withdrawn or otherwise removed to show the position of a stent graft 6 that was retained underneath the sheath 10.

The delivery device 2 has a guide wire catheter 3 which extends from a location distal of a handle 7 to and through a tapered nose cone dilator 11 at the proximal end of the device. The guide wire catheter 3 extends longitudinally through a passageway or lumen 5 of a positioner or pusher catheter 4 which is connected to a proximal end of handle 7. The guide wire catheter 3 may be fixed with respect to the pusher catheter 4 by a pin vice 12 at the distal end of the handle 7. A sheath 10 is disposed coaxially over and around a portion of the pusher catheter 4 (as best illustrated in FIG. 1) and extends from a distal end of the nose cone 11 to a sealing assembly and manipulator 14 attached about distal end 15 of the sheath 10. The sealing assembly and manipulator 14 may, in one example, be an automatically sealing valve comprising a hemostatic seal assembly including a silicone disc assembly.

Preferably, at least a portion of the delivery device 2, including the guide wire catheter 3 and sheath 10 near the proximal end 19 of the device is curved or otherwise has a curve imparted to a portion of it. The delivery device 2 may also be straight or straightened during use, such that it can conform to the tortious vasculature. Such a curved configuration may facilitate proper orientation of the delivery device 2 during delivery and deployment in a patient's vasculature. For example, such a curve or bend acts to orient the delivery device 2 in line with the curvature of the aorta 46 as illustrated generally in FIG. 8.

Figure 3:
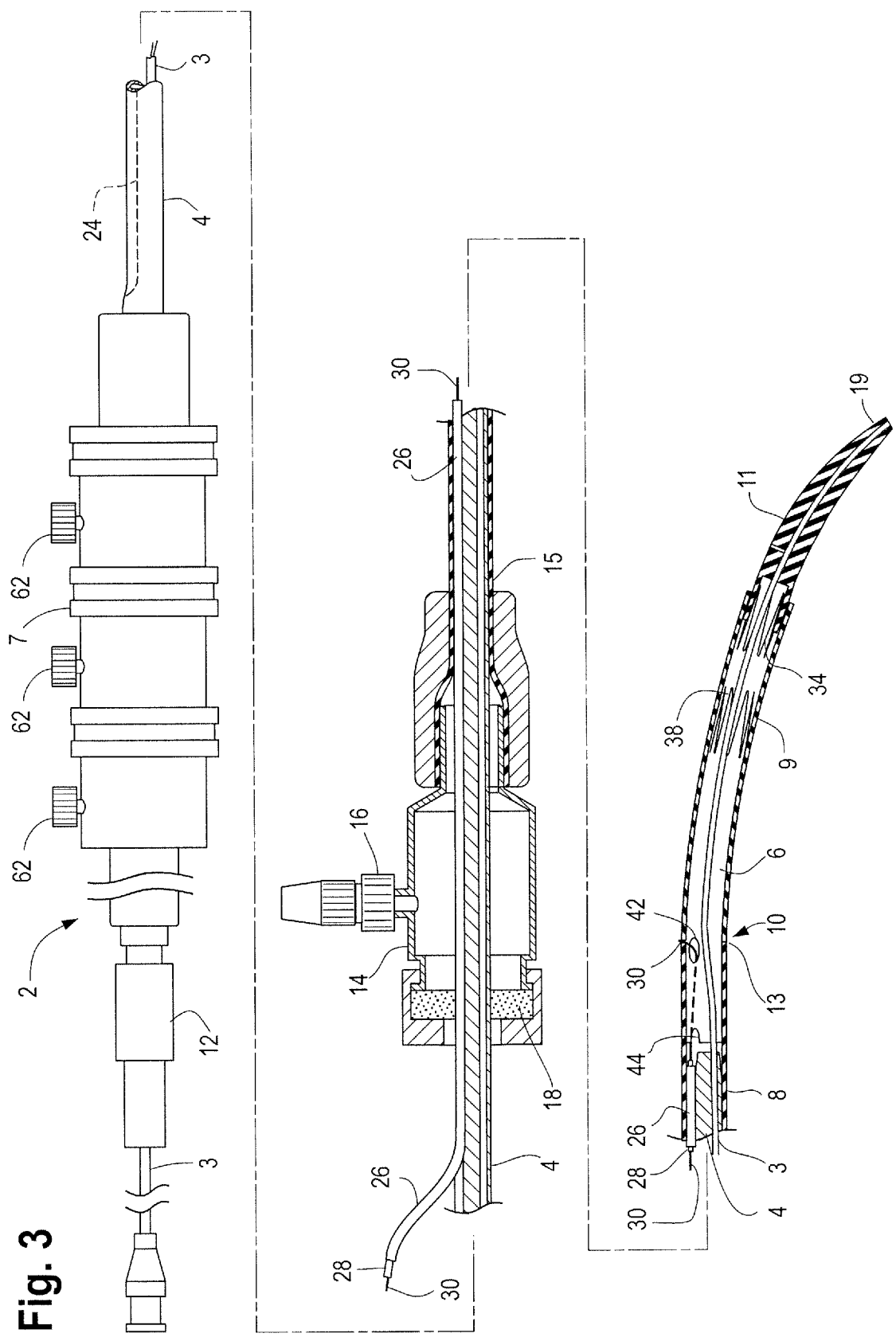
FIG. 3 shows a partial cross-sectional side view of the delivery device of FIG. 1 illustrating details of the stent graft covered by the sheath.
Figure 4:
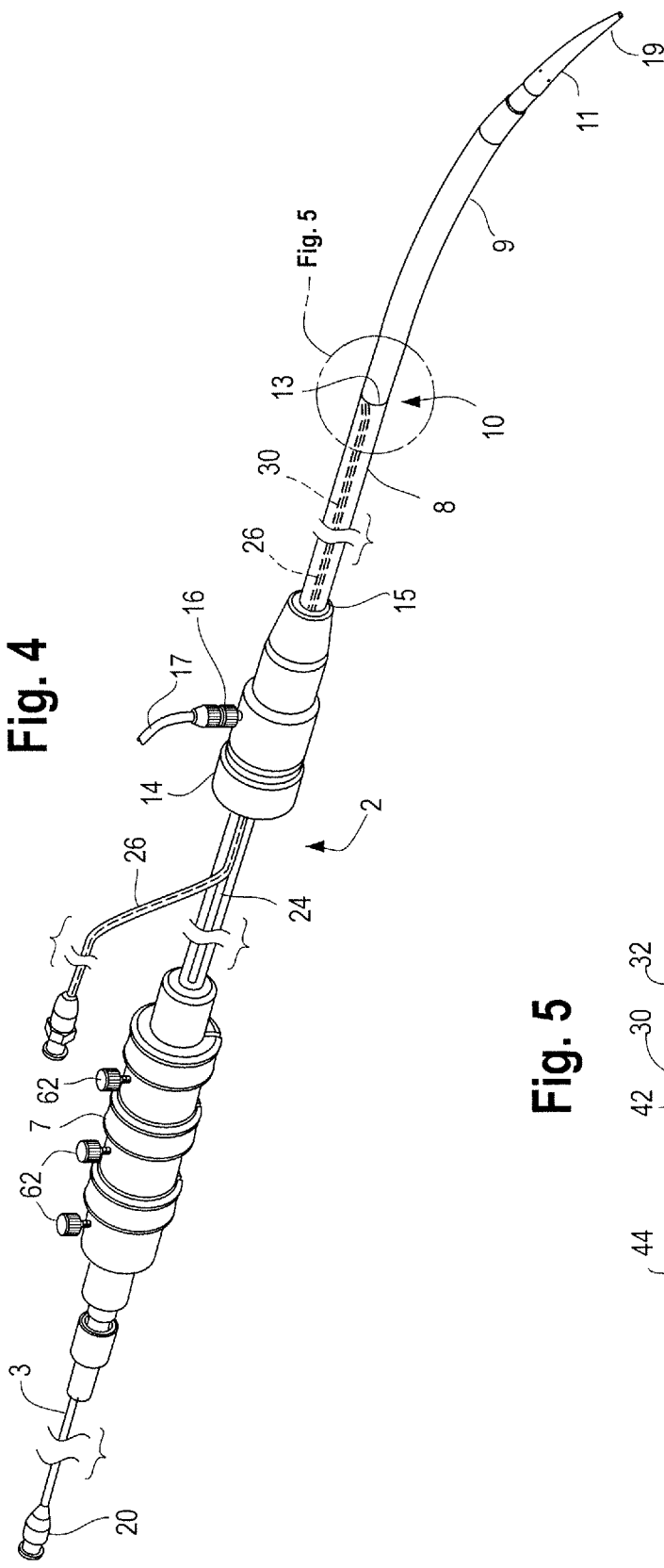
FIG. 4 is a perspective view of one example of a delivery device illustrating a pre-loaded auxiliary catheter and auxiliary guide wire extending along a portion of the device and under the distal sheath segment.

The sheath 10 extends proximally from the manipulator 14 to the nose cone dilator 11 and covers the stent graft 6 as is shown in FIGS. 1 and 3 during introduction of the delivery device 2 into a patient. As best illustrated in FIGS. 1 and 4, the sheath 10 includes a split 13 between its proximal and distal ends, thus forming a distal sheath segment 8 that meets the seal assembly 14 at the sheath's distal end 15 and a proximal sheath segment 9 that meets the nose cone 11 at the sheath's proximal end. The sheath 10 may be withdrawn or otherwise removed to expose the stent graft 6 (as shown in FIG. 2) during deployment when the delivery device 2 is in a selected position within the vasculature of a patient. Withdrawal of the sheath 10, and in particular, withdrawal of the proximal and distal sheath segments 8, 9 is described in further detail below. A Luer lock connector hub 20 may be attached at the distal end of the guide wire catheter 3 for connection to syringes and other medical apparatus (not shown).

The stent graft 6 is carried on the guide wire catheter 3 proximally of the pusher catheter 4 and distally of the nose cone dilator 11. As shown in FIG. 3, sealing assembly and manipulator 14 includes a silicone disk 18 which seals against the pusher catheter 4 for preventing the backflow of fluids there through. The disk 18 includes a slit for the insertion of the nose cone dilator 11 and pusher catheter 4. Sealing assembly and manipulator 14 also includes side arm 16 to which tube 17 is connected for introducing and aspirating fluids therethrough. Nose cone dilator 11 includes a tapered proximal end 19 for accessing and dilating a vascular access site over a guide wire 60 extending through the guide wire catheter as shown in FIG. 8 during placement in the vasculature.

As shown in FIGS. 1-4, along the length of the pusher catheter 4 from just proximal of the handle 7 to the proximal end of the pusher catheter 4 is preferably a longitudinal groove 24. An auxiliary catheter 26 is received into the groove 24. Through a lumen of the auxiliary catheter 26 extends an auxiliary dilator 28 and an auxiliary guide wire 30. The auxiliary catheter 26 may, in one example, be retained between the pusher catheter 4 and the sheath 10. For example, the auxiliary catheter 26 may extend from a location distal of the manipulator 14, through the silicone disk/rubber seal 18 to be sealed against the pusher catheter 4. Alternatively, the auxiliary catheter 26 may extend though a lumen 5 of the pusher catheter 4 parallel to the guide wire catheter 3. In such case, the proximal end portion of the pusher catheter 4, which may be a smooth tapered surface, may include an opening or aperture (not shown) through which the auxiliary catheter 26 can extend to exit the pusher catheter lumen 5 at or near the proximal end 22 of the pusher catheter.

As shown in FIGS. 1-4, the auxiliary catheter 26 extends longitudinally along a portion of the pusher catheter 4 and under the distal sheath segment 8. As shown in FIG. 4, the proximal end of the auxiliary catheter 26 then curves so that it runs substantially perpendicular to the longitudinal axis of the delivery device 2 just distal of the sheath split 13. As shown, the proximal end of the auxiliary guide wire 30 can then extend through the auxiliary catheter 26 and through the sheath split 13 between the proximal and distal sheath segments 8, 9 as illustrated in an enlarged view in FIG. 5. In one example, the auxiliary guide wire 30 may be pre-loaded so that it is part of the device (e.g., it extends at least partially through the auxiliary catheter 26) at the time of use, or alternatively, the auxiliary guide wire 30 may not be pre-loaded.

Turning now to FIGS. 3 and 6, the stent graft 6 carried on the delivery device 2 preferably comprises a main tubular body 32 of a biocompatible material. In one example, low profile (approximately 0.125 mm thickness) and ultra-low profile (approximately 0.080 mm thickness) graft materials make sheath sizes of 18-22 Fr. possible for a 38 mm device manufactured from low profile materials, or 14-18 Fr. for a 38 mm device manufactured from ultra low profile materials. The stent graft 6 has a first end 34 and a second end 36 and a plurality of stents 38 attached to the graft material. The term "stent" means any device or structure that provides, or is configured to provide, rigidity, expansion force, or support to a body part (e.g., a diseased, damaged, or otherwise compromised body lumen). A stent may comprise any suitable material, including, but not limited to, biocompatible metals and plastics. Examples of suitable materials include metals such as stainless steel and nitinol, and plastics such as polyethylene terephthalate ("PET"), polytetrafluoroethylene ("PTFE") and polyurethane. A stent may be "expandable," that is, it may be capable of being expanded from a constricted configuration to an expanded configuration. A stent may be self-expanding and thus, expand by virtue of its own resilience. Alternatively, a stent may be pressure-expandable and expand only upon the application of an external force (e.g., a balloon) and/or may be expandable upon application of heat, such as when exposed to body temperature. An example of a self-expanding stent is the Z-STENT®, which is available from Cook Incorporated, Bloomington, Ind., USA.

When the stent graft 6 is loaded onto and carried by the delivery device 2, the first end 34 of the stent graft 6 is closer to the proximal end of the delivery device 2 and the second end 36 of the stent graft 6 is closer to the distal end of the delivery device 2. When placed in the vasculature, the first (proximal) end 34 of the stent graft 6 may be located in the descending aorta while the second (distal) end 36 of the stent graft 6 may extend at least partially into the aortic arch 46.

Various mechanisms may be used to radially restrain the stent graft 6 on the delivery device 2 and also to ensure that the stent graft 6 conforms to the curvature of the vasculature, especially in the aortic arch 46. In one example, the first end 34 of the graft may be slanted to enhance conformance in a vessel. Optionally, sutures may be used to gather graft material on the inner curve of the stent graft 6 to further help enhance conformance to the curve of the vessel in which the stent graft 6 is placed. Also, diameter reducing ties or sutures may be placed on the first and/or second end of the stent graft during delivery to retain the stent graft 6 in a radially inwardly compressed configuration. When the diameter reducing ties and/or sutures are removed during deployment, the stent graft 6 is permitted to expand within the vessel lumen and seal against the vessel walls.

One or more of the stents 38 at the first and/or second ends of the graft may include barbs 40. Such barbs 40 may help anchor the stent graft 6 to the vessel wall and thereby limit migration or inadvertent displacement of the stent graft 6 within the vessel lumen, while also preventing possible crushing of any internal or external portions of the graft (such as the helical internal side branch, described below) that may result from the graft collapsing or kinking within the vessel.

Turning back to FIGS. 5 and 6, in one example, the stent graft 6 has at least one fenestration 42 formed in the main tubular body 32. The stent graft 6 also may include at least one scalloped fenestration 44 formed in the second end 36 of the stent graft 6. In one example, the stent graft 6 is preferably configured for placement in the aortic arch 46 and/or in the descending thoracic aorta, and the curvature of the proximal end of the delivery device 2 acts to orient the device and the stent graft 6 carried thereon within the vasculature, as shown in FIG. 8. The at least one fenestration 42 may be aligned with a branch vessel, such as the brachiocephalic 48, left subclavian 50 and/or left common carotid arteries 52, which are branch vessels extending from the aortic arch 46. There may be additional fenestrations formed in the main graft body 32, as desired, to align with additional branch vessels, to restore patency or otherwise provide flow thereto. As described in further detail below and illustrated in FIGS. 7 and 8, an external side branch or connection stent graft 54 may be deployed so that it is sealingly connected to and extends from the fenestration 42 and into a branch vessel, including but not limited to a brachiocephalic 48, left subclavian 50 and/or left common carotid artery 52. In the case of arch branch vessels which are generally located at the outer curve of the aorta 46, the fenestrations 42 and/or side branch stent-graft(s) 54 can be aligned with the greater curvature of the delivery device 2.

As shown in FIG. 8, an external side branch stent graft 54 extends from the fenestration 42 and into the left subclavian artery 50 to facilitate flow thereto. The scalloped fenestration 44 formed in the second end 36 of the main stent graft body 32 thus accommodates the ostium or opening into the left common carotid artery 52 so that when the main stent graft body 32 is placed in the aorta 46, flow into a branch vessel such as the left common carotid artery 52 and/or left subclavian artery 50 is not impeded and can continue through both the fenestration 42 and the opening provided by the scalloped fenestration 44. It is also contemplated that the main stent graft body 32 can be placed in other portions of the aorta such that the fenestration 42 aligns with other branch vessels in the aortic arch 46 (to allow deployment of an external side branch stent graft 54 therein, if needed) while the scallop 44 formed in the second end 36 of the main graft body 32 accommodates and allows flow to continue into other branch vessels when the main graft 6 is in place.

Extending from fenestration 42 towards the second end 36 of the main graft body 32 within the lumen of the main stent graft 6 is an internal side branch 56 defining a side branch lumen 58. The internal side branch may be constructed of the same material as the graft body 32, or alternatively, the internal side branch 56 may be constructed of a different material. The internal side branch 56 may be integrally formed with the main graft body 32 or it may be a separately formed branch that is attached to the main graft body 32 about fenestration 42 by sutures, adhesives or similar known attachment mechanisms. As illustrated in FIG. 6 and FIG. 9, the internal side branch 56 is preferably curved, such as in a helical shape, such that its unattached or free end curves around the scalloped fenestration 44. In other words, the helical shape of the internal side branch 56 avoids the scallop 44 formed in the second end 36 of the main graft 32. It will be appreciated that the internal side branch 56 may be of other shapes or configurations and/or extend from the fenestration 42 at varying angles in order to accommodate and extend around the scalloped fenestration 44 so as not to interfere with, block or otherwise impede the opening provided by the scallop 44. The lumen of an external side branch stent graft 54 that is sealingly connected with the fenestration 42 is preferably in flow communication with the lumen 58 of the internal helical side branch 56, as illustrated generally in FIGS. 6 and 8, so that flow through the main stent graft body 32 can also be directed though the lumen 58 of the internal side branch 56 and continue through the external side branch 54 and into a branch vessel (such as the common carotid artery 52 or subclavian artery 50, for example). The internal side branch 56 may also include one or more internal or external stents (not shown) secured to the graft to provide support and to help maintain the shape and configuration of the internal side branch 56.

Figure 5:
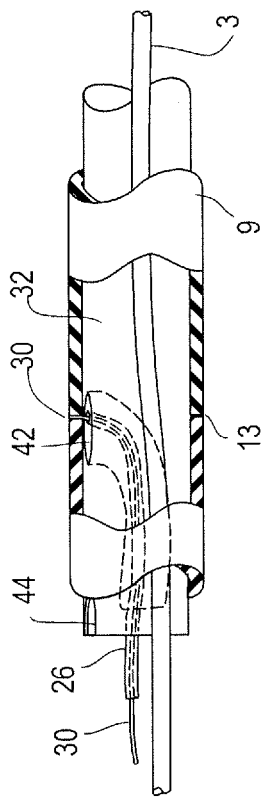
FIG. 5 is an enlarged view of the proximal end of the delivery device illustrating the split sheath with a proximal end of the auxiliary guide wire extending between the proximal and distal sheath segments.

As shown in FIGS. 4, 5 and 7, the auxiliary catheter 26 extends through a portion of the lumen of the main stent graft 32 and into the internal side branch 56 where it exits the internal side branch though the fenestration 42 formed in the main tubular body 32. Preferably, when the stent graft 6 is loaded onto the delivery device 2 and is retained underneath the sheath 10, the fenestration 42 formed in the main tubular body 32 is aligned with the split 13 in the sheath 10 as shown in FIG. 5. Thus, the proximal end of the auxiliary catheter 26 exits from the lumen 58 of the internal side branch 56 via the fenestration 42 and, with the fenestration 42 at least partially aligned with the split 13 in the sheath 10, the proximal end of the auxiliary catheter 26 can thereby extend through the sheath split 13 between the proximal and distal sheath segments 8, 9 as shown in FIGS. 5 and 7. An auxiliary guide wire 30 extends through the lumen of the auxiliary catheter 26 and can be moved longitudinally within the auxiliary catheter lumen. Thus, when the auxiliary guide wire 30 is moved proximally, the wire can be advanced through the split 13 in the sheath 10 and extend into a branch artery to facilitate cannulation thereof, as described further below.

Referring now to FIG. 8, in the process of deployment, a guide wire 60 is preferably inserted in a vessel, such as the right subclavian artery 64, with an introducer needle using known vascular access techniques. Delivery system sizes of approximately 18-20 Fr. or smaller may make delivery from the subclavian artery possible in some patients, which facilitates ease of placement of the guide wire 60 in the vessel lumen, especially when treating Type B dissection (a dissection being identified by reference number 66 in FIG. 8). The guide wire 60 may be advanced though and over the aortic arch 46 until it extends down into the descending aorta. One common practice is to use a through wire starting from the subclavian artery, snaring the wire from another location in the vasculature and pulling it out of the femoral artery. In this way, the subclavian approach may be used to facilitate cannulation of the vessel lumen, yet allow delivery of the device from the femoral approach. A transapical approach would also have similar benefits. It is also contemplated that the stent graft 6 could be loaded onto the delivery device in reverse and delivered from a femoral approach. Specific delivery system modifications (e.g., location of the pre-loaded components relative to the delivery device 2, length of the nose cone 11, and the like) could exist for each separate delivery approach, as necessary and desired.

Referring back to FIG. 8 and further describing one non-limiting example of a delivery method, the delivery device 2 may be tracked over the guide wire 60 and manipulated to the deployment site for the stent graft 6. As previously mentioned, the curved proximal end portion of the delivery device 2 assists in orienting the delivery device 2 within the aorta 46 as well as in orienting the stent graft 6 carried on the delivery device 2 at a target location within the aorta.

Once the graft 6 has been positioned in a desired location in aorta 46, the auxiliary guide wire 30 (which, if pre-loaded, has been extended through the fenestration 42 during preloading of the stent graft 6 onto the delivery device 2) can be manipulated to extend through the auxiliary catheter 26 so that it is advanced through the split 13 in sheath 10 to enter a left carotid artery 52 or left subclavian artery 50, for instance, and remain there while the stent graft 6 is still sheathed. The auxiliary dilator 28 can then be advanced over the auxiliary guide wire 30 until it enters the branch vessel. The auxiliary catheter 26 can then be advanced over the dilator 28 and the dilator 28 can then be withdrawn. Accordingly, the branch vessel is cannulated by the auxiliary catheter 26.

Alternatively, before withdrawal of the dilator 28 the auxiliary guide wire 30 can be withdrawn and a stiffer guide wire advanced through the dilator 28 and into the branch artery.

Once the branch vessel has been cannulated, the auxiliary catheter 26 may remain there, in position, during deployment of the main stent graft 6. In one example, to deploy the main stent graft 6, the sheath 10 is withdrawn. For example, the proximal sheath segment 9 may be pushed proximally together with the nose cone 11, until a first end 34 of the stent graft 6 is uncovered. The first end 34 of the stent graft 6 may then be expanded in the vessel lumen. The distal sheath segment 8 may be withdrawn distally, to uncover the remainder of the stent graft 6. If necessary, any diameter reducing ties and/or sutures at the first end 34 or second end 36 of the stent graft 6 may be released to allow stent graft 6 to fully expand and deploy within the vessel.

Following deployment of the stent graft 6, a further delivery device (not shown) for delivering an external side branch or extension stent graft 54 into the branch artery, for instance, can then be tracked over the auxiliary guide wire 30 through the auxiliary catheter 26 into the cannulated branch vessel. The extension graft 54 may then be deployed in the target branch vessel and either self-expand or be balloon expanded, if necessary. Preferably, the extension graft 54 is connected to the main stent graft 6 via an intermediate bridging stent graft (not shown), which may also be tracked over the auxiliary guide wire 30 to its desired location, until the bridging stent graft extends from fenestration 42 on one end and is secured to extension graft 54 at the opposing end. Alternatively, the extension graft 54 may be directly attached to the main stent graft 6 without a bridging stent graft. After the extension graft 54 is fully deployed within the desired branch vessel, the auxiliary catheter 26 and also the auxiliary guide wire 30 may be removed from the target vessel and withdrawn from the delivery device 2.

By this pre-catheterisation using an auxiliary catheter 26, auxiliary dilator 28 and/or auxiliary guide wire 30 extending through the helical internal side arm 56 and out through fenestration 42 while the stent graft 6 is still sheathed, the process of deployment of a side branch or extension stent graft 54 into a branch artery can be simplified and improved. In essence, the placement of the auxiliary catheter 26 between the proximal and distal sheath segments 8, 9 enables the pre-catheterisation of a branch artery before the main stent graft 6 is unsheathed and fully deployed in the aorta 46. This also allows for re-positioning, adjustment and alignment of the fenestration 42 and/or scallop 44 of the main stent graft 6 before unsheathing if necessary and desired.

The handle 7 at the distal end of the pusher catheter 4 remains outside a patient in use and includes one or more release mechanisms 62 used to release one or more trigger wires (not shown) which may be used to retain the first and/or second ends 34, 36 of the stent graft 6 onto the delivery device 2. Release of the trigger wire(s) allows a physician to selectively control the release of any suture(s) or diameter reducing ties that retain the stent graft 6 in a radially inward constricted configuration during delivery, such that the stent graft may subsequently expand within the vessel lumen when the trigger wires are removed and the diameter reducing ties are released. With trigger wires and/or diameter reducing ties removed, the main stent graft 6 can be then fully deployed and released from the device, and the entire delivery device 2 can be withdrawn from the patient's vasculature.

It can be seen that the delivery device 2 and stent graft assembly as described herein effectively and efficiently facilitates the introduction, placement and deployment of a stent graft assembly into one or more vessels in order to treat and/or restore patency to one or more of such vessels. It is also contemplated, however, that the disclosure is not so limited and may relate to delivery devices and stent grafts that are suitable for any vessel lumen in which treatment and repair thereof is necessary or desired.

Throughout this specification, unless the context requires otherwise, the words "comprise" and "include" and variations such as "comprising" and "including" will be understood to imply the inclusion of an item or group of items, but not the exclusion of any other item or group items. While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together.

The invention claimed is:

1. A system for the delivery and deployment of an endovascular stent graft comprising: a delivery device having a longitudinal axis comprising a pusher catheter having a proximal end and a distal end and defining a lumen extending between the proximal and distal ends and a guide wire catheter extending longitudinally within the lumen of the pusher catheter; a stent graft comprising a main tubular body of a biocompatible graft material and releasably coupled to the proximal end of the delivery device, a sheath having a proximal end and a distal end, wherein the sheath is disposed over the stent graft thereby retaining the stent graft in a radially contracted configuration on the delivery device, the sheath comprising a split located between the proximal and distal ends of the sheath thus forming a distal sheath segment located distal of the split and a proximal sheath segment located proximal of the split; wherein the stent graft comprises a proximal end and a distal end and a first fenestration located between the proximal and distal ends of the stent graft, and wherein the first fenestration is at least partially aligned with the split in the sheath when the stent graft is in the radially contracted configuration on the delivery device; a first mechanism for deploying the proximal sheath segment and a second mechanism for deploying the distal sheath segment; and an auxiliary catheter having a proximal end and a distal end and defining a guide wire lumen therebetween, wherein the auxiliary catheter extends longitudinally within a lumen formed by the distal sheath segment and through the sheath split between the proximal and distal sheath segments.

2. The system of claim 1 wherein the stent graft further comprises at least one scalloped fenestration formed in the graft material at at least one of the proximal and distal ends; an internal side branch defining a lumen and extending from the first fenestration towards at least one of the proximal and distal ends of the stent graft within a lumen of the graft, the internal side branch configured to extend at least partially around the at least one scalloped fenestration.

3. The system of claim 2 wherein the auxiliary catheter extends through the lumen of the internal side branch.

4. The system of claim 1 wherein a proximal portion of an auxiliary guide wire extends at an angle relative to the longitudinal axis of the delivery device.

5. The system of claim 1 wherein the proximal sheath segment is configured to be manipulated independently of the distal sheath segment.

6. The system of claim 1 wherein the stent graft further comprises a first end and a second end and wherein at least one stent is attached to the graft material at the first end and at least one stent is attached to the graft material at the second end.

7. The system of claim 6 wherein each of the at least one stents further comprises at least one barb.

8. The system of claim 1 wherein the stent graft is moveable from the radially contracted configuration to a radially expanded configuration.

9. The system of claim 1 wherein the stent graft further comprises diameter reducing ties on at least one of a first end of the stent graft and a second end of the stent graft.

10. The system of claim 1 wherein the stent graft is tapered such that the diameter of the stent graft decreases between a first end of the stent graft and a second end of the stent graft.

11. The system of claim 1 further comprising a second delivery device, the second delivery device comprising a second stent graft carried thereon, the second stent graft comprising a tubular body of a biocompatible graft material defining a main lumen.

12. The system of claim 11 wherein the second delivery device is configured to be advanced through the first fenestration formed in the main tubular body of the stent graft.

13. The system of claim 11 wherein the second stent graft carried by the second delivery device is configured to be positioned within a branch vessel extending from the aortic arch.

14. The system of claim 11 further comprising a sheath mounted coaxially over at least a portion of the second stent graft.

15. A stent graft assembly comprising: a stent graft comprising: at least one stent; a main tubular body of a biocompatible graft material defining a main lumen having a first end and a second end; at least one scalloped fenestration formed in the graft material and extending from an edge of the graft material at the second end; at least one additional fenestration formed in the graft material of the main tubular body, wherein the at least one additional fenestration generally aligns with the at least one scalloped fenestration on the graft body along a longitudinal axis; an internal side branch defining a lumen and extending from the at least one additional fenestration towards the second end of the stent graft within the lumen of the main tubular body; wherein the internal side branch comprises a helical configuration such that the internal side branch is configured to extend at least partially around the at least one scalloped fenestration, wherein a sheath is disposed over the stent graft thereby retaining the stent graft in a radially contracted configuration; the sheath comprising a split located between the proximal and distal ends of the sheath thus forming a distal sheath segment located distal of the split and a proximal sheath segment located proximal of the split; wherein the at least one additional fenestration is at least partially aligned with the split in the sheath when the stent graft is in the radially contracted configuration within the sheath.

* * * * *